(12) United States Patent
Rebec (10) Patent No.: US 9,649,056 B2
(45) Date of Patent: May 16, 2017

(54) ANALYTE SENSOR WITH EXTENDED RANGE OF DETECTION

(71) Applicant: Mihailo V. Rebec, Bristol, IN (US)

(72) Inventor: Mihailo V. Rebec, Bristol, IN (US)

(73) Assignee: Optica, Inc., Tigard, OR (US)

( * ) Notice: Subject to any disclaimer, the term of this patent is extended or adjusted under 35 U.S.C. 154(b) by 447 days.

(21) Appl. No.: 13/731,007

(22) Filed: Dec. 29, 2012

(65) Prior Publication Data

US 2013/0172699 A1    Jul. 4, 2013

Related U.S. Application Data

(60) Provisional application No. 61/581,572, filed on Dec. 29, 2011.

(51) Int. Cl.
*A61B 5/1455* (2006.01)
*A61B 5/1459* (2006.01)
*A61B 5/145* (2006.01)

(52) U.S. Cl.
CPC ........ *A61B 5/1459* (2013.01); *A61B 5/14532* (2013.01); *A61B 2560/0233* (2013.01)

(58) Field of Classification Search
CPC .................................................. A61B 5/1455
See application file for complete search history.

(56) References Cited

U.S. PATENT DOCUMENTS

| 6,251,083 | B1 | 6/2001 | Yum |
| 2005/0249633 | A1 | 11/2005 | Blatt |
| 2008/0188722 | A1* | 8/2008 | Markle et al. ............... 600/316 |
| 2009/0018418 | A1 | 1/2009 | Markle |

FOREIGN PATENT DOCUMENTS

| JP | 06-261890 A | 9/1994 |
| WO | WO2008-078128 A1 | 7/2008 |

* cited by examiner

*Primary Examiner* — Eric Winakur
*Assistant Examiner* — Marjan Fardanesh
(74) *Attorney, Agent, or Firm* — Schwabe Williamson & Wyatt, P.C.

(57) ABSTRACT

Embodiments provide sensors, such as implantable sensors, and methods of producing such sensors. An implantable sensor may include a base, one or more chambers, and one or more sensor reagents. A membrane may be coupled to the chambers over the sensor reagents. The implantable sensor may be at least partially implanted into the dermis of an animal. One or more of the sensor reagents may emit light or exhibit a color change in response to the presence of a target analyte or reaction product thereof. The response may be detected and analyzed by the user or by a reader device to determine the target analyte concentration.

32 Claims, 8 Drawing Sheets

ANALYTE SENSOR WITH EXTENDED RANGE OF DETECTION

CROSS REFERENCE TO RELATED APPLICATIONS

The present application claims priority to U.S. Provisional Patent Application No. 61/581,572 filed Dec. 29, 2011 and entitled "Analyte Sensor With Extended Range Of Detection," the entire disclosure of which is hereby incorporated by reference in its entirety.

TECHNICAL FIELD

Embodiments herein relate to the field of sensors, and, more specifically, to a long-term implantable sensor with an extended range of detection.

BACKGROUND

The continuous long-term monitoring of medical conditions such as diabetes presents challenges for both patients and medical care providers. Traditional methods that require the patient to repeatedly obtain and test blood or other fluids can be painful and inconvenient, and this may lead to reduced compliance on the part of the patient.

Implantable sensors have been developed to mitigate these drawbacks. However, implantable sensors currently used in continuous glucose monitoring devices suffer from a limited range of functionality. They are designed to measure glucose levels in the 40-400 mg/dL range or in the 150-600 range, but not both. If they do have a greater response range the resolution and accuracy are severely compromised. However, blood glucose analysis strip-based systems can be used to measure glucose levels that fall within either of those ranges. For this reason, and for overall performance limitations, current implantable sensor systems might not be considered by the FDA as an equivalent of a blood glucose strip-based system.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

DETAILED DESCRIPTION OF DISCLOSED EMBODIMENTS

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "N/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A) B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Embodiments herein provide sensors, such as implantable sensors, with an extended range of detection and methods of producing such implantable sensors. Sensors as described herein may be used to measure analyte levels over a wider range of analyte concentrations and/or with greater accuracy than prior implantable sensors. While the description below includes examples of implantable sensors, the term "sensor" is also intended to encompass sensors that are not configured for implantation, such as in-vitro sensors. Non-implantable sensors can be provided with extended ranges of detection in the same or similar manner as an implantable sensor, using the same or similar designs, modifications, and features discussed in reference to implantable sensors. In addition to extended detection ranges, such non-implantable sensors may have increased accuracy and precision. Non-implantable sensors with extended detection ranges may be used, for example, to test blood, plasma, serum, saliva, urine, or other biological fluids obtained from a test subject.

For the purposes of this description, an "implantable sensor" is a sensor that is implanted into the skin with the main body of the sensor residing in the dermis of the skin. In some embodiments, another portion of the implanted sensor may protrude into the epidermis, extending through the outer surface or to just below the surface of the skin. In other embodiments, the entirety of the implanted sensor may reside in the dermis. The implantable sensor may reside in the skin for a period of time that can range from one hour to a couple of years depending upon one or more factors, such as the type(s) of analysis needed and the stability of the analysis components. In some embodiments, an implantable sensor may be retained in the body of a subject for at least a minute. In other embodiments, an implantable sensor may be configured to reside in the body of a subject (e.g., in the skin) for at least one month. In still other embodiments, an implantable sensor may be configured to reside in the body of a subject for a duration of time such as a week, a month, 2-4 months, 3-6 months, or more than 6 months.

For the purposes of this description, a "response" is a change exhibited by an implantable sensor or portion thereof (e.g., in an analysis region) upon exposure to a target analyte/parameter. A "response" can be, but is not limited to, a shift in wavelengths absorbed, a shift in wavelengths deflected, an emission of light, a change in the intensity of light deflected/reflected/emitted (e.g., spectral intensity, radiant intensity spectral power, radiance, or spectral radiance), or any other measurable change in deflected/reflected/emitted light. A "response" can also be a value that is representative of such a change. In some embodiments, some or all of the wavelengths may be in the visible range. In other embodiments, some or all of the wavelengths may be in the infrared range. A "response" can be a color or color change.

For the purpose of this description, the term "subject" includes humans as well as non-human animals.

For the purpose of this description, the term "color" includes colors within the visible spectrum and colors not visible to the human eye (e.g., infrared).

For the purposes of this description, a "range of detection" of an implantable sensor is the full set of concentrations, amounts, or levels of target analyte/parameter to which an implantable sensor or portion thereof (e.g., an analysis region) is operable to exhibit a response. A range of detection may have an upper limit and a lower limit. In contrast, a "range of response" is the full set of changes (or values representative thereof) that an implantable sensor or portion thereof is operable to exhibit upon exposure to the target analyte/parameter at all concentrations/levels/amounts. The range of response may also include an upper limit and a lower limit. An upper or lower limit of a range of detection may be expressed, for example, as a concentration, level, or amount of a target analyte/parameter. Optionally, such a value may be expressed as a function of fluid or tissue volume (e.g., mg/dL). An upper or lower limit of a range of response may be expressed, for example, in terms of wavelength(s), color shift, absorbance, reflectance, change in wavelength spectrum, spectrum shape, light emission, or intensity of light emitted.

For the purposes of this description, "coextensive" ranges are ranges that have substantially similar or identical upper limits and/or lower limits, or in which at least half of the values of one range are included within another range. In contrast, "contiguous" ranges are ranges in which fewer than half of the values within one range are included within the other range(s). Contiguous ranges may overlap to some degree, or may have a common boundary (e.g., the upper limit of one range may be substantially similar or identical to the lower limit of the other range). The term "contiguous" may also be used in reference to a collective series of three or more ranges where the first and second ranges are "contiguous" (e.g., 20-200 units and 200-450 units) and the second and third ranges are "contiguous" (e.g., 200-450 units and 450-700 units), etc.

In one embodiment, an implantable sensor may have a base and/or a body defining one or more chambers, at least one analyte reagent system with one or more sensor reagents, and one or more permeability/blocking members. The base may be constructed from one or more materials such as a polymer or a metal. The body may be coupled to a surface of the base. The chamber(s) may be one or more gaps, wells, or voids extending partially or fully through the thickness of the base/body. An analyte reagent system, or one or more sensor reagents thereof, may be retained within a chamber. One or more permeability/blocking members may be coupled to the chamber(s) and/or to the base/body. In some embodiments, one or more of the sensor reagents are retained between the permeability/blocking member(s) and the base/body. The analyte reagent system may be configured to respond to the presence of an analyte by changing color and/or emitting light (luminescence). The response may be exhibited in proportion to the concentration of the analyte.

The sensor may be implanted within or below the skin of a subject. The analyte reagent system may respond to the presence of the target analyte by producing a color change (e.g., a change in the wavelengths absorbed/reflected by the sensor), emission of light, and/or a change in the intensity of light reflected, deflected, or emitted by the sensor. The response may be read with a reading device that has an optical sensor (e.g., a camera). The optical data acquired by the optical sensor may be converted to an analyte concentration, such as a blood glucose value.

The sensor may have multiple analysis regions. An analysis region may include an analyte reagent system. The analyte reagent system may be disposed within a chamber or a portion thereof, and/or coupled to a portion of the sensor (e.g., coupled to the base). An analysis region may exhibit a response, such as a change in color or electrical current generated, upon exposure to the target analyte that is present at a concentration within the range of detection of the analysis region. Optionally, the analysis region may also include the underlying base and/or one or more permeability/blocking member(s). Thus, in some embodiments, a first chamber may be part of a first analysis region, a second chamber may be part of a corresponding second analysis region, and a third chamber may be part of a corresponding third analysis region. Alternatively, in other embodiments, a chamber may include, or may be part of, more than one analysis region. For example, a sensor may have a single chamber and the reading device may select multiple areas/portions across/along the single chamber to read. These selected areas may vary by location, size, and number, resulting in a potentially infinite number of analysis regions.

An analysis region may exhibit a response, such as a change in color or emission of light, upon exposure to the target analyte that is present at a concentration within the range of detection of the analysis region. One or more of the analysis regions may be a reference or control region configured for use in calibration of the reader device (e.g., an optical sensor) and/or correction of a measured or calculated value. For example, an analysis region may provide a reference or control that can be used by the reader device to correct for differences in circulation and/or diffusion changes. Some correction or calibration areas may be parts of the sensor base, body, or other component, rather than an analysis region. Correction or calibration areas provided in or on parts of the sensor may be used, for example, to determine optical corrections for differences in light intensity, skin pigmentation, skin scattering, or image exposure times, and/or differences in the depth of the sensor in the skin (e.g., for a sensor that is placed at a greater or lesser depth in the skin than recommended).

Some or all of the analysis regions may have contiguous ranges of detection and coextensive ranges of response. Thus, two or more analysis regions may exhibit different responses (e.g., different colors) within a common range of response (e.g., between orange and blue), and a given response may represent a different target analyte concentration in each of those analysis regions. For example, the upper limit of the detection range of a first analysis region may be approximately the same as, or may overlap, the lower limit of the detection range of a second analysis region. Upon exposure to the same concentration of the target analyte, the first and second analysis regions may exhibit different responses. For example, at a particular target analyte concentration, the first analysis region may be blue in color and the second analysis region may be green or orange in color. Similarly, a particular color or other response in the first analysis region may represent a different target analyte concentration than the same response in the second analysis region. For example, the first analysis region may exhibit a blue color at one concentration of the target analyte, but the second analysis region may exhibit a blue color at a different concentration of the target analyte.

In some embodiments, ranges of response may be ranges of colors/wavelengths within the visible spectrum. In other embodiments, ranges of response may include colors/wavelengths beyond the visible spectrum (e.g., one or more colors/wavelengths in the infrared range). For example, an analysis region may exhibit a maximum response in the infrared range. This may allow improved detection of the response, due to the lesser absorption of wavelengths within this range by the tissues surrounding the analyte sensor.

In one embodiment, the implantable sensor is configured such that one analysis region exhibits a change to a given analyte concentration while another analysis region exhibits no change/response. In one example of such a configuration, two or more analysis regions may have contiguous detection ranges that do not overlap. Thus, a particular analyte concentration may be within the detection range of only one analysis region, which exhibits a response. Alternatively, two or more analysis regions may have contiguous detection ranges that overlap, and only one of the two or more analysis regions may exhibit a response where the target analyte concentration falls within the detection range of that analysis region but is not within the detection range of the other analysis region(s) (i.e., the target analyte concentration falls outside the overlapping area of the detection ranges).

In another embodiment, the implantable sensor is configured such that two or more analysis regions may exhibit a substantially simultaneous change in response to the same target analyte concentration. For example, two or more analysis regions may have contiguous detection ranges that overlap, and may exhibit substantially simultaneous responses to an analyte concentration that falls within the overlapping portion of the detection ranges. Alternatively, two or more analysis regions may exhibit substantially simultaneous changes in response to a target analyte concentration, and the change in one of the analysis regions may indicate that the target analyte concentration is outside the detection range of that analysis region. For example, an analysis region may exhibit a response that is at or near the upper or lower limit of the range of response (e.g., a blue color or an orange color, or an emission of light at an upper or lower limit of an intensity range), indicating that the target analyte concentration falls outside of the detection range of that analysis region.

An implantable sensor may have two, three, four, five, six, seven, eight, nine, ten, or more than ten analysis regions with contiguous ranges of detection and coextensive ranges of response. Some analysis regions may be defined by sensor structure. For example, in some sensors, each analysis region may correspond to a portion of the sensor that is physically defined by a barrier or space, such as a chamber separated from another chamber by a vertical wall. Other analysis regions may be defined by the reader device based on a pre-determined pattern, a captured image of the sensor or sensor response, or previous sensor readings (e.g., previous images or previously determined representative values). For example, a sensor may include a single continuous chamber with a reagent gradient and/or membrane gradient. As another example, a sensor may have some analysis regions defined by sensor structure (e.g., separate chambers) and other analysis regions defined by the reader device (e.g., separate analysis regions in one or more of the separate chambers).

The sensor may exhibit different responses in different areas due to variations in analyte permeability, depth, surface area, structure, and/or sensor reagent types or concentrations within or among the chamber(s). The reader device may determine a detection range for one or more of the analysis regions based on factors such as the location of the analysis region relative to some portion of the sensor (e.g., an end or edge, another analysis region, an orientation mark or other feature), a previously determined detection range for a corresponding portion of the sensor, and/or a pre-determined pattern stored or accessed by the reader device. The reader device may determine a representative value for the target analyte(s) based on the responses of the analysis regions and their corresponding detection ranges.

Such implantable sensors may be operable to detect a target analyte or parameter over a broader range and/or with greater accuracy than prior sensors. The coextensive ranges of response may allow the implantable sensor to be read by a device that detects or measures responses within a common response range. Such reader devices may be less complex and/or less expensive to produce than reading devices configured to operate over multiple ranges.

Analysis regions may be provided with different functional ranges through a variety of design modifications. One such design modification may include modifying the chemical composition of multiple analysis regions in order to optimize the corresponding concentration ranges within which each of the analysis regions operates. This may include varying the relative amounts or concentrations of sensor reagents (e.g., chromoionophores and/or ionophores that shift the color change associated with a particular target analyte concentration) or using different sensor reagents in different areas of the sensor (e.g., different ionophores and/or chromoionophores in different areas). This type of modification may also include varying the types and amounts of buffering reagents in the corresponding areas.

Another option is to modify the permeability of each analysis region to the target analyte or reagent(s). For example, analysis regions may have one or more corresponding permeability layers that permit entry of a target analyte into the corresponding analysis area. The permeability layer(s) may be modified or adjusted among different analysis regions to alter the permeability of each analysis region to the target analyte. This may be done, for example, by varying the thickness of a permeability/blocking member, varying the cross linking of the permeability/blocking member, and/or using permeability/blocking members with different compositions between one or more of the sensor reagents and the target analyte(s). Thus, one analysis region may be more permeable to a target analyte than another analysis region, and may receive a greater number of analyte molecules than the other analysis region during a given period of time. In some examples, two or more design modifications (e.g., modification of chemical composition and modification of permeability layers) may be used in combination within the same sensor.

A reader device may detect the responses of multiple analysis regions. In some examples, the reader device may also convert the acquired data into a representative value (e.g., a target analyte concentration, a non-target control analyte concentration, a color, a temperature, a pressure, etc.), compare the detected responses or values to one another, compare the detected responses or values to previous responses or values, display a representative value, and/or alert a sensor user of the representative value. In some examples, the reader device may alert a sensor user or a user of the reader device of a possible sensor malfunction.

Alternatively, the sensor may be used without a separate reader device. For example, the responses may be detected and evaluated visually by a user. A visual aid such as a chart may be provided with representative values that correspond to various responses within the range of response of the analysis regions. The user may visually detect a response, locate the response or nearest equivalent on the chart, and read the corresponding representative value to determine the concentration or level of the target analyte. The use of multiple analysis regions may provide a visual qualitative assessment that is more accurate that assessments based on a single analysis region. For example, a sensor that provides color changes in a plurality of analysis regions may allow users to translate the sensor responses to more accurate glucose values than sensors with only one analysis zone. In addition, sensors with multiple analysis regions as described herein may be used more easily/accurately by color-blind individuals; while the individual may be unable to see a particular color in a single analysis region, he/she can view/interpret differences among multiple analysis regions (e.g., a pattern of lighter and darker shades As indicated above, one or more of the analysis regions and/or portion of the sensor may be or include a control region(s). A control region may provide a reference, such as a color or shape, for calibration of the reader device. In some examples, a control region may be a duplicate of another analysis region (i.e., may detect the same target analyte within the same range of detection and have the same range of response). The reader device may compare the responses of the two regions, and determine whether the two responses are the same within a margin of error. If a difference between the two responses is determined to exceed the margin of error, the reader device may determine that the reading is inaccurate and/or that the sensor is malfunctioning. Alternatively, the reader device may average the responses from the two regions and determine a representative value for the target analyte (or non-target control analyte) based on the determined average. Optionally, the reader device may determine that a response or value from one of the two regions exceeds a predetermined threshold/value, differs from an average or other selected value by more than a predetermined limit, or is outside a particular range, such as an expected range. In response, the reader device may disregard that response or value. For example, the reader device may exclude that response/value when determining a representative value for the target analyte (or non-target control analyte).

Alternatively, a control region may detect another analyte or condition, such as an analyte or condition that is typically present at relatively constant levels within the dermis. Examples of such analytes include, but are not limited to, sodium, potassium, pH, creatinine, uric acid, chloride, and cholesterol. The reader device may read the control/reference region and compare the acquired data to previous readings. If a difference between the readings is determined to exceed a margin of error, the reader device may determine that the reading may be inaccurate and/or that the sensor is malfunctioning.

As still another alternative, a control region may be configured to exhibit a response to a non-target analyte, and the response may be used by the reader device to correct or determine representative values for a target analyte based on a local condition such as local blood/fluid flow. For example, a control region may be configured to detect a non-target analyte that is administered to a subject. Optionally, the non-target analyte may be administered with a drug, a treatment, or a dose of the target analyte. The time at which the non-target analyte is administered may be entered into the reader device. The reader device may read the control region continuously or at timed intervals for some period of time. The control region may exhibit a response to the non-target analyte. The reader device may correct or determine a representative value for a non-target analyte as a function of the length of time between the administration of the drug/treatment and the detection of the analyte by the control region. Optionally, the reader device may determine that the length of time exceeds a predetermined limit and alert the sensor user or reader device user of a condition such as poor circulation or possible sensor malfunction. As another option, the response time may be used to determine and/or correct for a sensor lag time, such as a difference between the length of time required for the sensor to detect an analyte (e.g., a drug, treatment, or other analyte) in the dermis and the length of time required for the analyte to be detected in an analysis of whole blood, plasma, or other fluid(s).

Implantable sensors may have one or more indicators for various purposes, such as for confirmation of sensor integrity or calibration of the reader device. These controls may be features on or within the sensor. For example, a sensor may be provided with a component or portion that has a fixed color. The reader device may adjust one or more representative values based on the difference between the color of the indicator prior to insertion and the color of the indicator after insertion in order to compensate for differences in skin tone or depth of implantation.

Figure 1A:
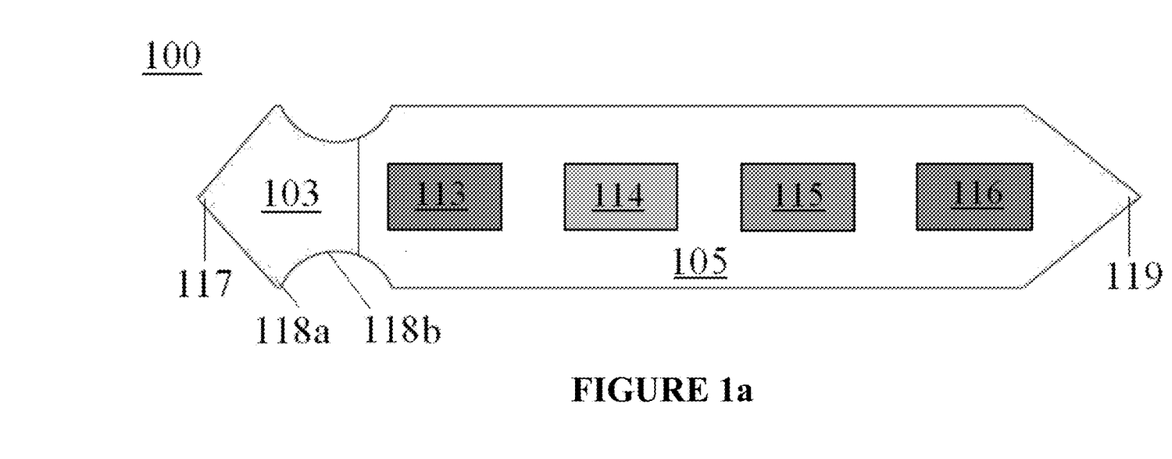
FIGS. 1a and 1b illustrate plan views of implantable sensors with an extended range of detection, in accordance with various embodiments.

FIGS. 1a-b and FIGS. 2a-d illustrate plan views and side views, respectively, of implantable sensors with an extended range of detection in accordance with various embodiments. As shown in FIG. 1a, an implantable sensor 100 may have a base 103 and a body 105 coupled to base 103. Base 103 and body 105 may form first and second layers, respectively, of implantable sensor 100. Alternatively, body 105 and base 103 may be formed as integral portions of a single unit (see e.g., FIGS. 1b and 2b). For example, body 105 and base 103 may be a single piece formed by molding, thermoforming, vacuum forming, compaction and sintering, cutting, or extrusion of a base material.

Analysis regions 113, 114, 115, and 116 may be arranged along base 103 and at least partially surrounded by body 105. While the illustrated example includes four analysis regions, other sensors may have two, three, five, six, seven, eight, nine, ten, fifteen, twenty, or more than twenty analysis regions. Some of the analysis regions may be provided with an analyte reagent system, including one or more sensor reagents, for analyzing the target analyte(s). One or more of the analysis regions may be configured to serve as a control for calibration and/or to confirm correct positioning, functionality, and/or accessibility of implantable sensor 100 to the target analyte(s) or control analyte(s).

Base 103 may have an elongate shape with a first end 117 and an opposite second end 119. One or both of first end 117 and second end 119 may terminate in a point or other shape to aid penetration into the skin during implantation. Base 103 may include one or more surface or edge features configured to enhance the retention of implantable sensor 100 within the dermis after implantation, such as projections 118a and/or invaginations 118b (FIG. 1a). These features may provide resistance to backward-directed pulling forces to prevent the dislocation of the implantable sensor after implantation. The surface or edge features may be disposed along any portion of base 103, such as near first end 117, near second end 119, along the bottom surface of base 103, along an upper surface of base 103 or body 105, or along an edge of base 103 or body 105. Surface or edge features may be added before, during, or after forming/coupling base 103 and body 105.

In some embodiments, second end 119 may be inserted into the dermis of a subject and first end 117 may be retained externally, above the epidermis, for removal. For example, the terminal edge (e.g., 0.5 mm) of first end 117 may protrude from the surface of the skin. In other embodiments, first end 117 may be positioned within the epidermis a short distance below the outer surface of the skin, and may become exposed for removal 1, 2, 3, 4, 5, or 6 months after implantation. In still other embodiments, first end 117 may be positioned below the epidermis after implantation. Alternatively, first end 117 may be inserted into the dermis of a subject and second end 119 may be retained externally (above the epidermis), within the epidermis, or below the epidermis as described above.

Figure 1B:
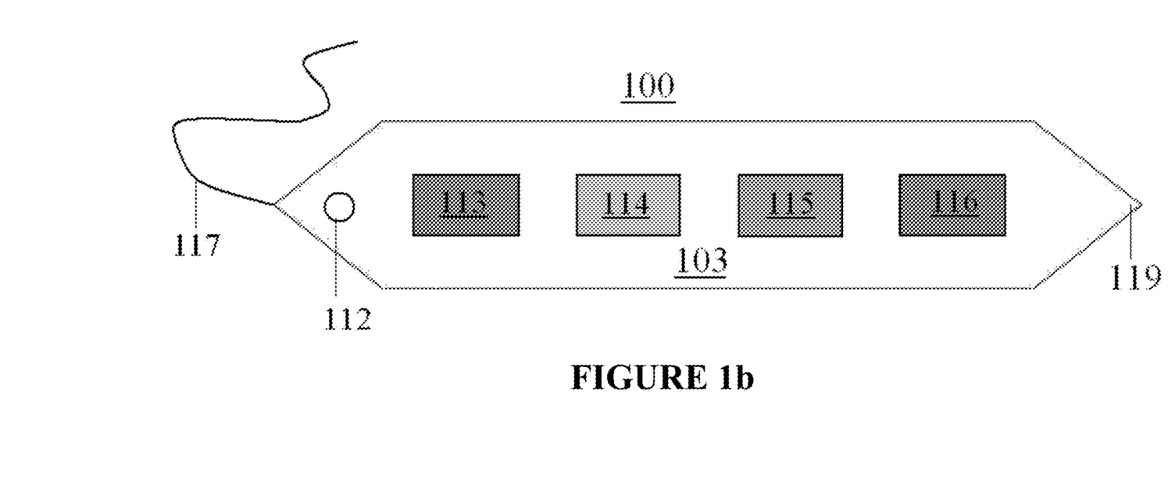

In some sensors, first end 117 may be a relatively thin and flexible member, such as a narrow tape or string, which can be grasped and pulled to remove the sensor from the skin (FIG. 1b). Other sensors may lack an elongated end. Optionally, a sensor may have a surface feature configured to mate with a portion of a removal device for removal of the sensor. For example, a sensor may be provided with a hole 112 through a portion of the base and/or body (FIG. 1b). A portion of an insertion/removal device may be inserted through the hole and pulled to remove the sensor from the skin. Some sensors may be configured to at least partially fold or collapse for removal.

Base 103 can include one or more materials such as a metal and/or metal alloy (e.g., stainless steel), a hydrogel, a plastic or polymer, a biopolymer (e.g., a polyanhydride), ceramic, and/or silicon. Examples of plastics or polymers may include, but are not limited to, polyacrylic acid (PAA), cross-linked polyethylene (PEX, XLPE), polyethylene (PE), polyethylene terephthalate (PET, PETE), polyphenyl ether (PPE), polyvinyl chloride (PVC), polyvinylidene chloride (PVDC), polylactic acid (PLA), polypropylene (PP), polybutylene (PB), polybutylene terephthalate (PBT), polyamide (PA), polyimide (PI), polycarbonate (PC), polytetrafluoroethylene (PTFE), polystyrene (PS), polyurethane (PU), polyester (PEs), acrylonitrile butadiene styrene (ABS), poly (methyl methacrylate) (PMMA), polyoxymethylene (POM), polysulfone (PES), styrene-acrylonitrile (SAN), ethylene vinyl acetate (EVA), and styrene maleic anhydride (SMA).

Base 103 may have a thickness in the range of 30 µm to 500 µm. For example, base 103 may have a thickness in the range of 30-35 µm, 35-40 µm, 40-50 µm, 50-60 µm, 60-70 µm, 70-80 µm, 80-100 µm, 100-150 µm, 150-200 µm, 200-250 µm, 250-300 µm, 300-350 µm, 350-400 µm, 400-450 µm, or 450-500 µm.

In some sensors, ambient light may be reflected by reagents within chambers 107, and the resulting diffuse reflection signal may be measured by a reader device. Optionally, base 103 may include a reflective material that is integral (i.e., integrated within the material used to form base 103) or provided in the form of a coating along one or more surfaces of base 103, such as a coating along the bottom surface. The inclusion of reflective materials in or on base 103 may reduce background effects from tissue below the sensor and/or enhance the reflection or transflection of light from by the sensor. At least some ambient light may pass through the reagents within chambers 107 to be reflected by the reflective material of base 103. The resulting transflectance signal may be measured by a reader device. In such examples, the sensor may provide diffuse reaction signals and transflectance signals, and the reader may measure the signals of one or both types. In one example, base 103 includes a strip of polyimide material impregnated with titanium dioxide ($TiO_2$). Optionally, base 103 may be thicker at a first end than at a second, opposite end, to provide an optical gradient.

Body 105 may be constructed from a variety of materials depending on the strength and permeability desired. In some examples, body 105 may be a plastic or a polymer (e.g., polyimide). Body 105 may range in thickness from 5 µm to 50 µm thick. For example, body 105 may have a thickness in the range of 5-10 µm, 10-15 µm, 15-20 µm, 20-25 µm, 25-30 µm, 30-35 µm, 35-40 µm, 40-45 µm, or 45-50 µm.

In one example, base 103 includes a strip of polyimide material impregnated with $TiO_2$, and body 105 is constructed from polyurethane. Body 105 can be applied onto base 103 as a liquid solution or vapor by printing (e.g., screen printing or inkjet printing), roll-coating, dip-coating, spin coating, spraying, chemical/physical vapor deposition, sol-gel, or other known methods. In some examples, the solution or vapor may be applied indiscriminately to an area of base 103. A pattern mask or other physical/chemical blocking agent may be used to prevent deposition of the solution or vapor over the areas where chambers 107 are desired. In other examples, the solution may be applied selectively/discontinuously to some areas of base 103, leaving other areas (e.g., chambers 107 and/or first end 117) untreated. Alternatively, body 105 may be a pre-formed solid, semi-solid, or gel, and may be coupled to base 103 with an adhesive. In some embodiments, body 105 and base 103 are formed as a single unit. Base 103 and/or body 105 can have varying thicknesses.

As best viewed in FIGS. 2a-d, one or more chambers 107 may extend partially or entirely through the thickness of body 105. One or more sensor reagents may be retained within chambers 107. Sensor reagents may be deposited in the form of a gel, liquid, solid, or semi-solid containing one or more membranes, beads, fibers, and/or other matrices to which at least some of the sensor reagents are bound. Sensor reagents may be deposited into the chambers by known methods such as screen printing, inkjet deposition, or micro deposition with nano or micro volume liquid deposition systems.

Chambers 107 may be cut from body 105 before or after body 105 is applied or coupled to base 103. Alternatively, body 105 and base 103 may be a single unit with chambers 107 made during formation of the unit (e.g., as part of a molding process) or after formation of the unit (e.g., by cutting or otherwise removing material from the unit). In the illustrated example, each of the four analysis regions 113, 114, 115, and 116 includes a corresponding chamber 107.

The number, shape, depth, and spatial arrangement of chambers 107 may vary among embodiments. Similarly, the shape and depth of chambers 107 may vary within an individual sensor, with some chambers having a greater depth or different shape than others. In the illustrated examples (FIGS. 1a-2d), the implantable sensor has four rectangular areas (i.e., chambers 107) that may be, for example, 800 um×400 μm in size. In other examples, an implantable sensor may have 2, 3, 4, 5, 6, 7, 8, 9, 10, or more than 10 chambers 107. Chambers 107 may have a variety of shapes (e.g., round, oblong, polygonal) in various combinations. Chambers 107 may have one or more tapered sides.

One or more of chambers 107 may contain an analyte reagent system with sensor reagents, discussed further below with reference to FIG. 3. Sensor reagents may be bound to microscopic beads, fibers, membranes, gels, or other matrices in various combinations. Some sensor reagents may be retained between membranes, bound to membrane materials coated onto a membrane, or coupled to or immobilized on a hydrophilic matrix. The analyte reagent system may be provided in a single layer or in multiple layers. For example, an analyte reagent system may include two, three, four, five, six, seven, eight, nine, ten, or more than ten layers.

At least one of the layers may be a permeability/blocking member, such as a membrane or a gel, which is selectively permeable to one or more sensor reagents, analytes, or reaction products. Examples of permeability/blocking members are described in U.S. Pat. No. 7,964,390, which is hereby incorporated by reference in its entirety. Permeability/blocking members may include one or more membranes, such as cellulose acetate membranes, cellulose acetate phosphate membranes, cellulose acetate phthalate membranes, and/or polyurethane membranes. Other permeability/blocking members may include, for example, a hydrogel, polyurethane, polyvinylpyrrolidone, acrylic polyesters, vinyl resins, fluorocarbons, silicones, rubbers, chitosan, hydroxyethylmethacrylate (HEMA), and/or polyhydroxyethylmethacrylate.

Figure 2A:
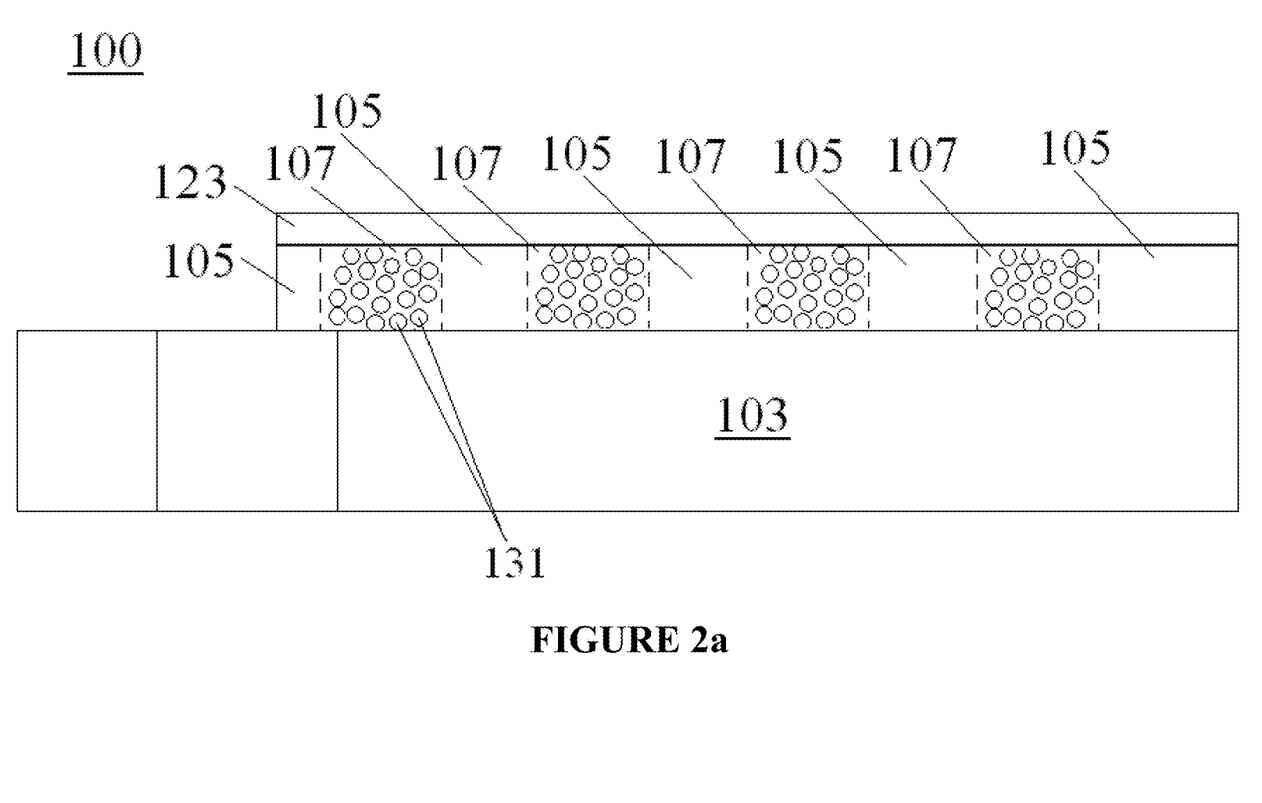
FIGS. 2a-d illustrate side views of implantable sensors with an extended range of detection, in accordance with various embodiments.

Permeability/blocking members may be applied individually to chambers 107 as separate units. Alternatively, permeability/blocking member 123 may be coupled to multiple chambers 107 as a single unit, as shown in FIG. 2a. This may provide neighboring chambers 107 with different permeabilities to a target analyte or reagent. In some examples, permeability/blocking member 109/123 may include one, two, three, four, five, or more than five membranes in a stacked or layered arrangement.

Different permeability/blocking member configurations and/or analyte reagent systems may be used in two or more chambers to provide analysis regions with contiguous ranges of detection. For example, referring to FIGS. 1b and 2b, analysis regions 113 and 116 may have a "low" detection range, analysis region 114 may have a "medium" detection range, and analysis region 115 may have a "high" detection range. The permeability/blocking members 109 may be more permeable to the target analyte in analysis regions 113 and 116 than in analysis region 114, and less permeable to the target analyte in analysis region 115 than in analysis region 114. Similarly, referring to FIGS. 1a and 2a, a permeability/blocking member 123 may have different configurations at different locations along its length, such as differences in pore size(s), thickness, or other parameters that influence permeabilities to a target analyte or reagent. Analysis regions 113, 114, and 115 may have different or modified analyte reagent systems instead of, or in addition to, different permeability/blocking member configurations. Optionally, the permeability/blocking member and/or analyte reagent system of one analysis region (e.g., analysis region 116) may be configured to detect a control or non-target analyte, such as sodium or potassium.

One or more of the layers may comprise a liquid or gel. In some embodiments, the liquid (or a liquid component of the gel) may be provided by the surrounding tissue after implantation of the sensor. For example, a layer may include one or more gel components in a dehydrated form, such as a powder, that is configured to form a gel upon exposure to tissue fluids.

Figure 2B:
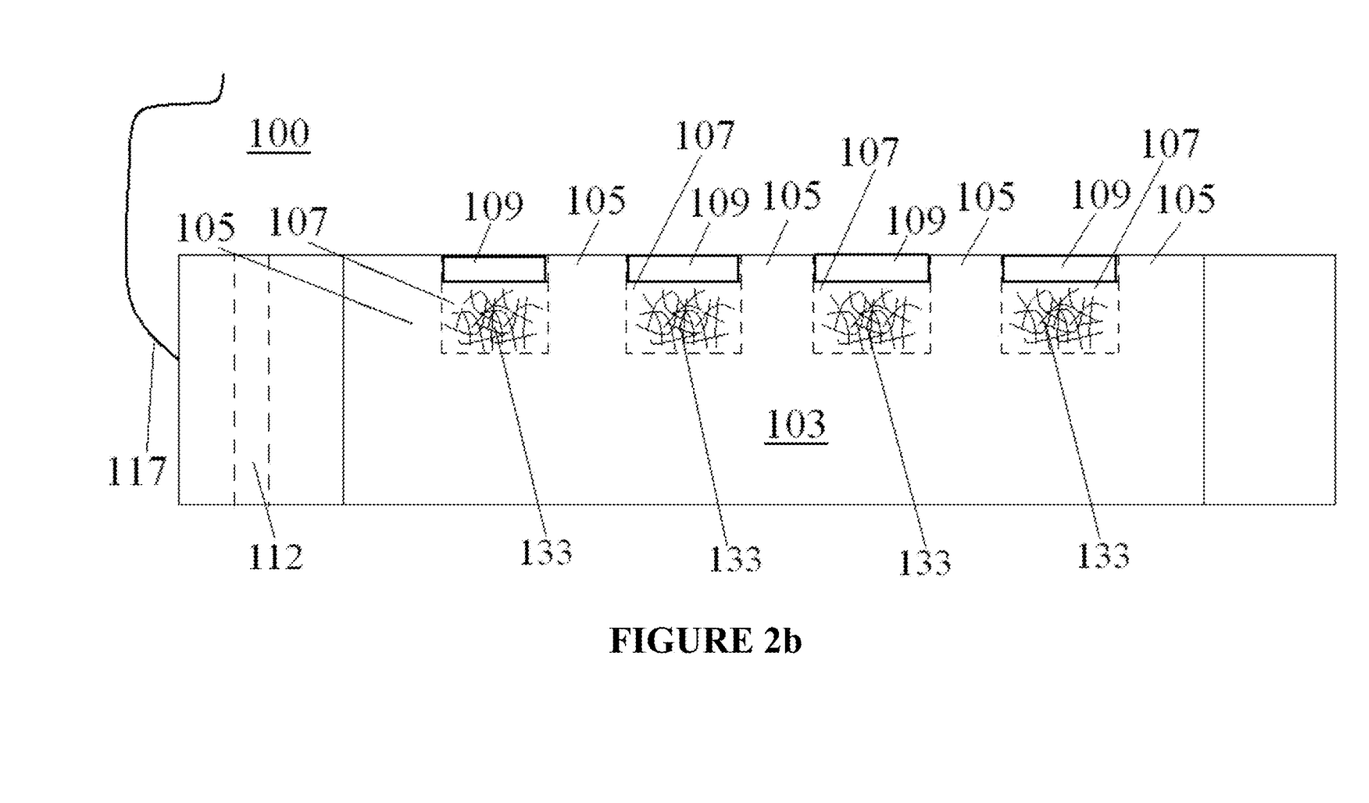
Figure 2C:
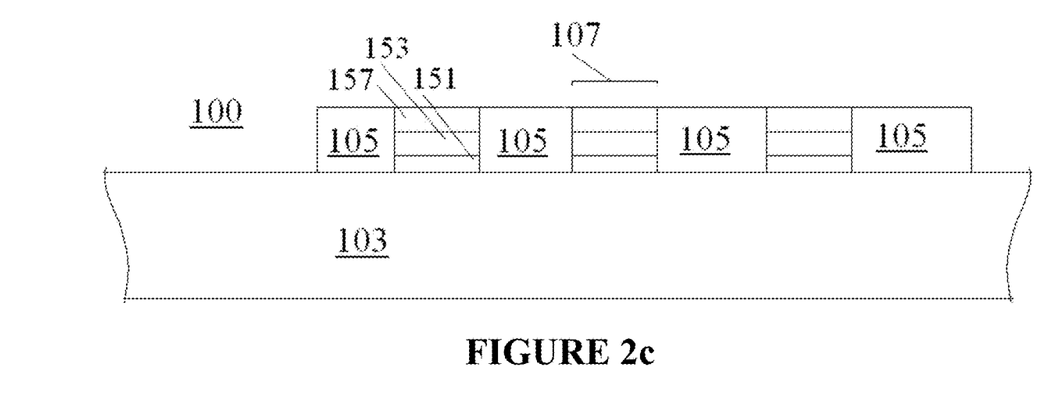

FIG. 2c illustrates an embodiment in which the analyte reagent systems of the implantable sensor are arranged in a first layer 151, a second layer 153, and a third layer 157. First layer 151 may include a matrix and an indicator. The matrix may include one or more of a liquid, a gel, beads, fibers, a membrane or membrane component(s), and/or another porous material. Some of the sensor reagents may be dispersed in the matrix or bound to a component thereof. The indicator may be a group of sensor reagents configured to collectively exhibit a response, such as a color change or emission of light, upon exposure to a target analyte.

In some embodiments, the indicator may be a pH sensitive dye that produces a color change or other detectable change in response to a change in pH resulting from a target analyte or reaction product/intermediate. The indicator may return to its previous color when the pH returns to its previous level. For example, as illustrated in FIG. 3, an indicator may include one or more of an ionophore, a lipophilic anion, and a chromoionophore (i.e., a lipophilic hydrogen ion sensitive dye). The ionophore may extract the ion to be detected (e.g., hydrogen), causing the chromoionophore to change color. Electrical neutrality may be maintained by the negatively charged anion. In other embodiments, an indicator may be a luminescent reagent that emits light in response to a target analyte or reaction product/intermediate. Luminescent reagents may include, but are not limited to, photoluminescent (e.g., phosphorescent or fluorescent), chemiluminescent, electroluminescent, electrochemiluminescent, or bioluminescent reagents. In still other embodiments, the indicator may be a pH sensitive agent that exhibits a response in the infrared range. Alternatively, an indicator may be an enzyme or reaction product thereof. Some embodiments may include two or more indicators in the same or different analysis regions.

In some examples, the matrix may be a membrane and the indicator may be immobilized on the membrane. In other examples, some of the indicator reagents may be bound to a matrix component, such as beads 131 (FIG. 2a) or elements 133 (e.g., fibers, a membrane, a membrane component, or other porous material; FIG. 2b). Other indicator reagents may be bound to separate membranes, beads, or other matrix components, or to different portions of the same matrix component.

Second layer 153 may be coupled to first layer 151. Second layer 153 may include a detection reagent. A detection reagent is a reagent that reacts with, or catalyzes a reaction of, the target analyte to produce a reaction product or intermediate. A detection reagent may be an enzyme or an enzyme system. For example, a detection reagent for glucose detection may be glucose oxidase ("GOX"), and a detection reagent for lactose detection may be lactase. In some embodiments, a detection reagent may be or include an antibody that binds to an analyte or reaction product, and/or an enzyme attached to such an antibody. The binding of the antibody to the analyte or reaction product may cause a change in the activity of the enzyme, which may influence or cause a change in pH. Thus, an analyte reagent system can include any antibody, enzyme, antibody-enzyme complex, or indicator known in the art for use in the detection of analytes in vitro or in vivo.

Second layer 153 may include a liquid, a gel, beads, fibers, a membrane or membrane component(s), and/or another porous material. In some examples, second layer 153 may include a membrane that is selectively permeable to a target analyte. The membrane may be impermeable to one or more sensor reagents (e.g., detection/indicator reagents). A detection reagent may be immobilized on a membrane, beads, or other element of second layer 153.

Third layer 157 may be a permeability/blocking member, as discussed above, that is configured to selectively limit the passage of a target analyte or interfering compounds into second layer 153. A permeability/blocking member may include one or more membranes and/or gels, alone or in combination.

Figure 2D:
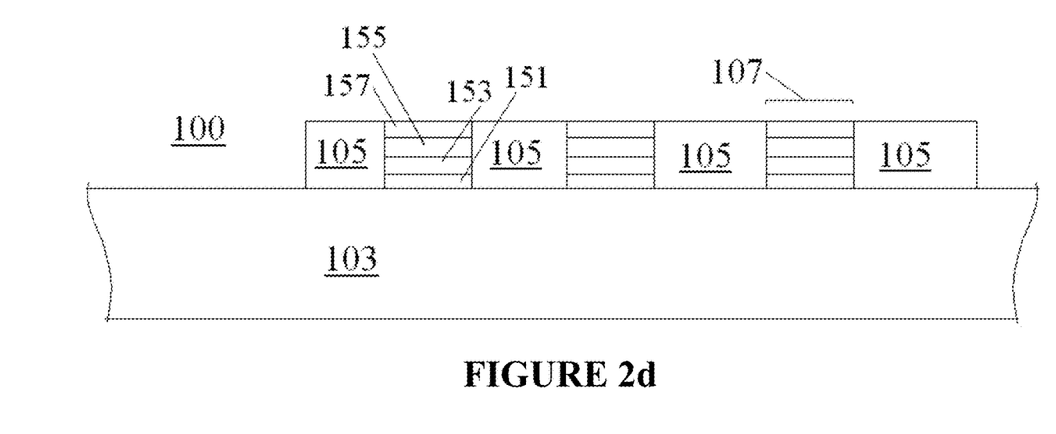

Optionally, as shown in FIG. 2d, a fourth layer 155 may be applied to reduce or prevent damage to another layer during manufacturing. For example, fourth layer 155 may be applied over first layer 151, and second layer 153 may be applied over protective layer 155. This may protect first layer 151 from being damaged as second layer 153 is being applied.

Figure 3:
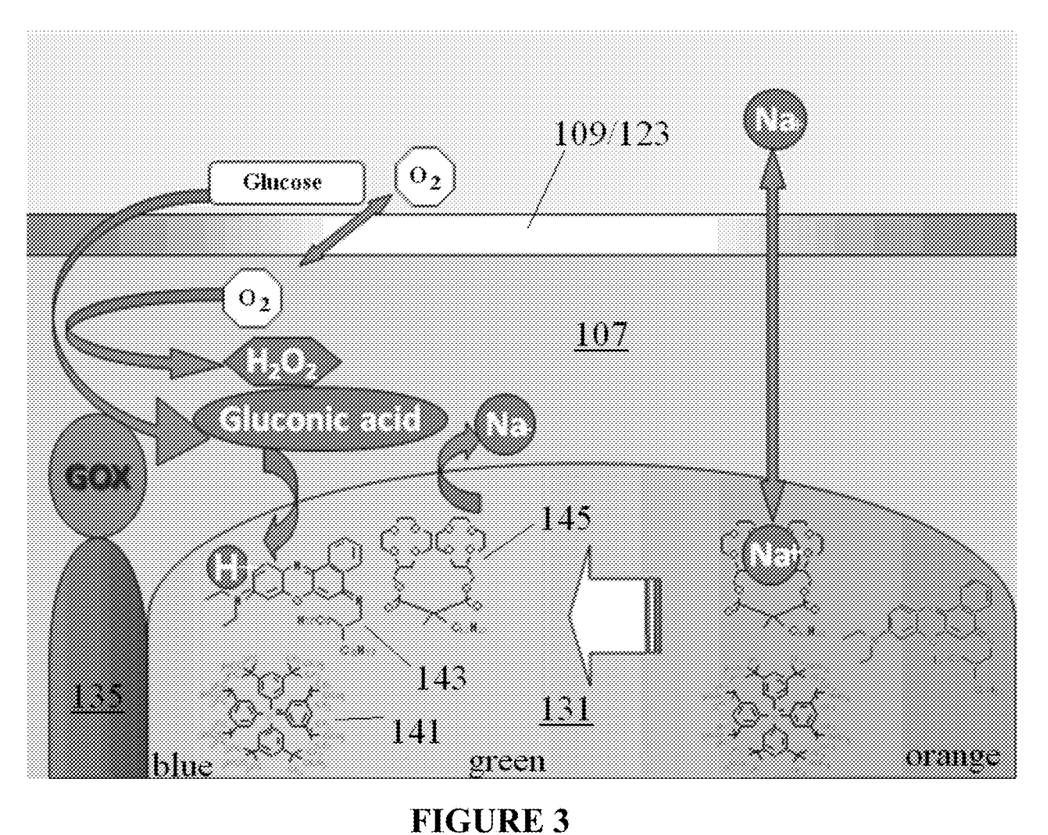
FIG. 3 illustrates an example of a reagent system for glucose detection in an implantable sensor with an extended range of detection.

In other embodiments, some or all of the detection reagent(s) and indicator(s) may be provided within a single layer (see e.g., FIGS. 2a, 2b, and 3). The indicator and detection reagent may be immobilized within the layer on beads, membranes, fibers, or other elements. A permeability/blocking member 109 may be coupled to the chambers 107 and/or to the body 105, and the detection reagent and indicator may be retained between the permeability/blocking member 109 and the body 105. In some examples, the detection reagent and/or indicator may be bound to the underside of the permeability/blocking member 109. Optionally, permeability/blocking member 109 may include two or more layers of membrane and/or gel.

As discussed above, an analyte reagent system may include an indicator and a detection reagent. The concentrations, amounts, or chemical compositions of one or more of these reagents may vary among chambers to provide analysis regions with contiguous detection ranges and coextensive ranges of response.

Some indicators may be pH-sensitive dyes with one or more chromoionophores, lipophilic anions, and/or ionophores. Examples of chromoionophores include, but are not limited to: chromoionophore I (9-(diethylamino)-5-(octadecanoylimino)-5H-benzo[a]phenoxazine) designated ETH5249; chromoionophore II (9-dimethylamino-5-[4-(16-butyl-2,14-dioxo-3,15ioxaeicosyl)phenylimino]benzo[a]phenoxazine) designated ETH2439; chromoionophore III (9-(diethylamino)-5-[(2-octyldecyl)imino]benzo[a]phenoxazine), designated ETH 5350; chromoionophore IV (5-octadecanoyloxy-2-(4-nitrophenylazo)phenol), designated ETH2412; chromoionophore V (9-(diethylamino)-5-(2-naphthoylimino)-5H-benzo[a]phenoxazine); chromoionophore VI (4',5'-dibromofluorescein octadecyl ester) designated ETH7075; chromoionophore XI (fluorescein octadecyl ester) designated ETH7061; and combinations thereof. Other indicators may include luminescent reagents, enzymes, and/or reaction products.

Examples of lipophilic anions include, but are not limited to: KTpClPB (potassium tetrakis(4-chlorophenyl)borate), NaHFPB (sodium tetrakis[3,5-bis(1,1,3,3,3-hexafluoro-2-methoxy-2-propyl)phenyl]borate), sodium tetrakis[3,5-bis(trifluoromethyl)phenyl]borate, sodium tetrakis(4-fluorophenyl)borate, combinations thereof, and the like.

Examples of ionophores include, but are not limited to: Sodium ionophores, such as bis[(12-crown-4)methyl]2-dodecyl-2-methylmalonate, designated ETH227; N,N',N"-triheptyl-N,N',N"-trimethyl-4,4',4"-propylidynetris(3-oxabutyramide), designated ETH157; N,N'-dibenzyl-N,N'-diphenyl-1,2-phenylenedioxydiacetamide, designated ETH2120; N,N,N',N'-tetracyclohexyl-1,2-phenylenedioxydiacetamide, designated ETH4120; 4-octadecanoyloxymethyl-N,N,N',N'-tetracyclohexyl-1,2-phenylenedioxydiacetamide), designated DD-16-C-5; 2, 3:11,12-didecalino-16-crown-5), bis(benzo-15-crown-5), and combinations thereof; Potassium ionophores, such as: bis[(benzo-15-crown-5)-4'-methyl]pimelate, designated BME 44; 2-dodecyl-2-methyl-1,3-propanedil bis[N-[5'-nitro(benzo-15-crown-5)-4'-yl]carbamate], designated ETH1001; and combinations thereof; Calcium ionophores, such as: (−)-(R, R)—N,N'-bis-[11-(ethoxycarbonyl)undecyl]-N,N'-4,5-tetramethyl-3,6-dioxaoctane-diamide), designated ETH129; N,N,N',N'-tetracyclohexyl-3-oxapentanediamide, designated ETH5234; N,N-dicyclohexyl-N',N'-dioctadecyl-3-oxapentanediamide), designated K23E1; 10,19-bis[(octadecylcarbamoyl)methoxyacetyl]-1,4,7,13,16-pentaoxa-10,19-diazacycloheneicosane), and combinations thereof.

FIG. 3 illustrates an example of an analyte reagent system with a pH-sensitive indicator for use in an implantable sensor. This reagent system provides a GOx/pH based reaction that produces a color shift (i.e., a variation in reflected wavelengths of light) that can be measured to determine a glucose concentration. In this example, the chromoionophore is chromionophore III, the ionophore is bis[(12-crown-4)methyl]2-dodecyl-2-methylmalonate, and the lipophilic anion is sodium tetrakis[3,5-bis(1,1,1,3,3,3-hexafluoro-2-methoxy-2-propyl)phenyl]borate trihydrate. The chromoionophore exhibits a pH-dependent color between the extremes of orange and blue. The pH shifts in response to varying concentrations of glucose. The reflected wavelengths (orange, yellow, green, blue) from the analysis regions can be detected and analyzed to determine the local glucose concentration.

As illustrated, glucose and oxygen enter chamber 107 through permeability/blocking membrane (109/123). Chamber 107 may include an indicator coupled to a substrate 131. In the illustrated example, the indicator includes a chromoionophore 143, an ionophore 145, and a lipophilic anion 141. A detection reagent (e.g., GOx) may be immobilized on a substrate 135. Each of substrates 131 and 135 may be an independent component such as a bead, a membrane, a fiber, or a surface of body 105 that is exposed within chamber 107. In other examples, a substrate 131 and a substrate 135 may integrated within one component.

The GOx converts glucose and oxygen to gluconic acid and hydrogen peroxide. Increasing production of gluconic acid causes a shift in pH. The chromoionophore 143 accepts a hydrogen ion, which causes a shift in the color of the chromoionophore 143 toward blue. As electrical neutrality is maintained by the lipophilic anion 141, the ionophore 145 responds to the acceptance of the hydrogen ion by releasing a sodium ion to maintain the charge balance. As the production of gluconic acid decreases, the ionophore accepts a sodium ion, and the chromoionophore releases a hydrogen ion, causing a shift in color of the chromoionophore toward orange. The shift in color causes a corresponding shift in wavelengths reflected by the analysis regions, which can be detected to monitor glucose levels at desired time intervals.

Optionally, one or more additional reagents may be provided within chamber 107. The additional reagent(s) may be provided to increase the rate of a chemical reaction, stabilize one or more components of the analyte reagent system, and/or convert a reaction product to another product. For example, catalase may be provided to convert hydrogen peroxide to water and oxygen.

In one embodiment, the above-described analyte reagent system may be provided in an implantable sensor for use in monitoring glucose levels in vivo. Referring again to FIGS. 1a-b, by way of example, analysis regions 113 and 116 of analyte sensor 100 may be configured to exhibit a color change in response to a blood glucose level within a first "low" range (e.g., 20 to 200 mg/dL). Analysis region 114 may be configured to exhibit a color change in response to a blood glucose level within a second "medium" range (e.g., 150 to 400 mg/dL or 150 to 450 mg/dL). Analysis region 115 may be configured to exhibit a color change in response to a blood glucose level within a third "high" range (e.g., 400 to 700 mg/dL). Thus, a blood glucose level of 200 mg/dL would be at the upper end of the detection range for analysis regions 113 and 116, at the lower third of the detection range for analysis region 114, and below the detection range for analysis region 115. Therefore, at this blood glucose level, analysis regions 113 and 116 would exhibit a blue color, analysis region 114 would exhibit a green color, and analysis region 115 would exhibit an orange color.

A reader device may detect and analyze the responses of the analysis regions to determine a blood glucose level/value. The reader device may also compare the responses of analysis regions 113 and 116 or assess other control values as described above to calculate the blood glucose level/value, determine a correction for the blood glucose level/value, and/or determine whether the sensor may be malfunctioning.

As discussed above, one or more design modifications may be used to provide an extended range of detection in an implantable sensor. FIGS. 4a-b and 5a-d illustrate examples of sensor configurations with such modifications. With reference to these figures and the corresponding description, a "sensor assembly" is an implantable sensor or a portion thereof.

Figure 4A:
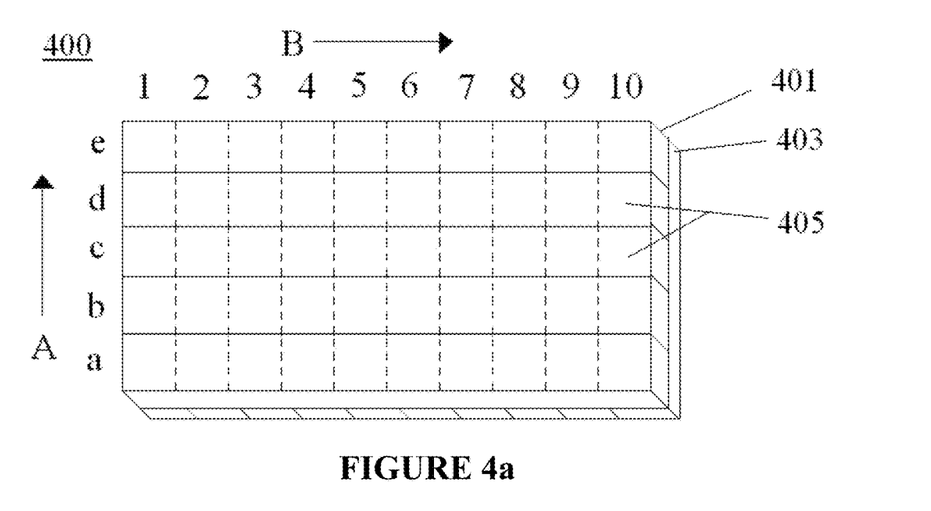
FIGS. 4a-b illustrate an example of an implantable sensor configuration.

As shown in FIG. 4a, a sensor assembly 400 may include a first component 401 and a second component 403. Each of first component 401 and second component 403 may be or include a portion of a chamber, a permeability/blocking member such as a membrane or gel, or a sensor reagent system. For example, first component 401 may be a permeability/blocking member and second component 403 may be a reagent system.

Figure 4B:
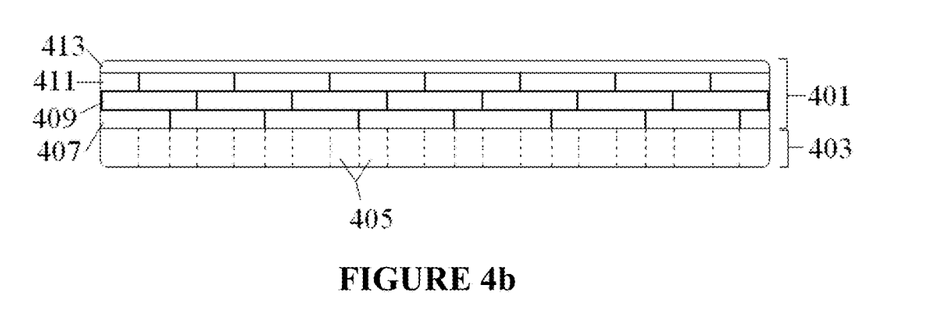

First component 401 may provide a first gradient extending in a first direction (Arrow A). The gradient may be continuous or discontinuous. Here, the first gradient may be a target analyte permeability gradient resulting from variations in the composition and/or thickness of first component 401. For example, first component 401 may be a permeability/blocking member with pores that decrease in diameter from one side ("a") to the opposite side ("e"). First component 401 may include an asymmetric membrane/gel that provides a continuous target analyte permeability gradient. Alternatively, first component 401 may include a lateral array of membranes/gels of varying configurations that provides a discontinuous target analyte permeability gradient. In some examples, first component 401 may include a combination of overlapping, vertically stacked, and/or laterally arrayed membrane/gel portions. FIG. 4b illustrates a side view of a sensor assembly in which first component 401 includes a stack of four layers 407, 409, 411, and 413 with varying gradients/configurations, resulting in variations in analyte permeability among analysis regions 405. In other examples, the first gradient may be a result of variations in the thickness, hydrophobicity, or reagent composition/concentration of first component 401.

Second component 403 may provide a second gradient extending in another direction (Arrow B). Again, the gradient may be continuous or discontinuous. The second gradient may be a sensor reagent concentration gradient, with reagent concentrations that progressively decrease from one end ("1") to the opposite end ("10"). Alternatively, the second gradient may be formed by varying the types, concentrations, or combinations of sensor reagents, the buffering system or buffer reagent concentrations, and/or the configuration of a medium or layer surrounding or supporting one or more of the sensor reagents.

Upon exposure to a target analyte, the sensor may exhibit a response that appears as a color change gradient, with different gradations of color change in different areas. The reader device may capture an image of the response and select areas of the image for analysis. In some examples, the reader device may assign a detection range to a particular zone or area of the image based on one or more factors such as the permeability and/or sensor reagent configuration of the corresponding area of the sensor. Alternatively, the reader device may be provided with a pre-determined detection range pattern to be applied to the image, or determine a detection range pattern based on a calibration process and/or prior sensor readings. The reader device may analyze the response (e.g., color or intensity) of each selected area as a function of the corresponding detection range. The reader device may then determine a representative value for the target analyte(s) based on the image data.

Referring again to FIG. 4a by way of example, a reader device may be provided with a pattern of pre-determined analysis regions 405 (e.g., e1, b3, c6, etc.). The reader device may capture an image of the sensor and select at least some of the areas of the image that correspond to the pre-determined analysis regions. The reader device may determine the concentration of a target analyte by identifying the analysis region in which a particular response (e.g., color or intensity), or the closest approximation thereof, appears. Alternatively, the reader device may refer to a look-up table of detection ranges for the pre-determined analysis regions and analyze two or more of the selected areas based on the corresponding detection ranges. The reader device may then determine a representative value for one or more target analytes based on the analysis.

In some embodiments, the reader device may select areas of the image based on color, intensity, or other factors. The selected area may correspond to an analysis region or to a portion of an analysis region. In some embodiments, the reader device may select multiple areas corresponding to different portions of the same analysis region. For example, the reader device may subdivide one or more of the analysis regions and analyze the corresponding portions of the image separately. The reader device may subdivide the image, or otherwise determine the number of areas to be selected, based at least in part on the quality of the captured image (e.g., whether exposure/resolution are sufficient). Optionally, the reader device may increase or decrease the size of a selected area based on image resolution. The reader device may determine/analyze the response of each of selected area separately.

The reader device may determine a representative value for the target analyte(s) based on one or more factors such as the size, number, shapes, locations, color, intensity, and/or pattern of the areas selected. In some embodiments, the reader device may determine a value (e.g., a representative value or for each of the selected areas. Values may then be averaged to reach a representative value for the analysis region. Optionally, the reader device may determine that one or more of the representative values differs from the others by more than a predetermined margin of error, and may discard that value. The redundancy provided by analyzing multiple areas within an analysis region may provide improved accuracy, resolution, and/or error detection.

Figure 5A:
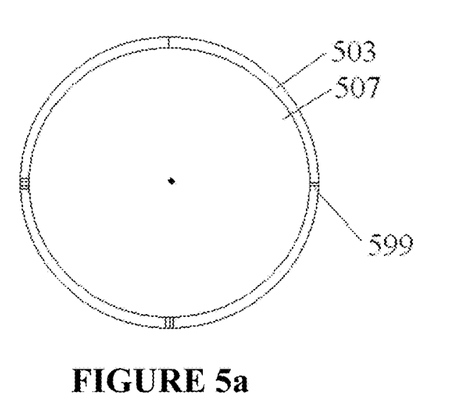
FIGS. 5a-d illustrate another example of an implantable sensor configuration.
Figure 5B:
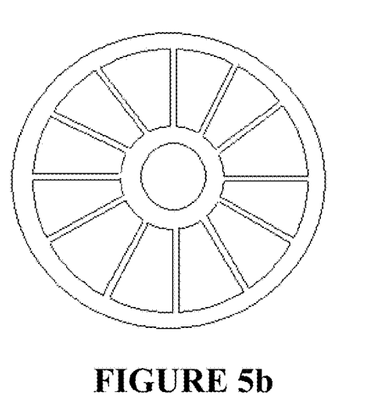
Figure 5C:
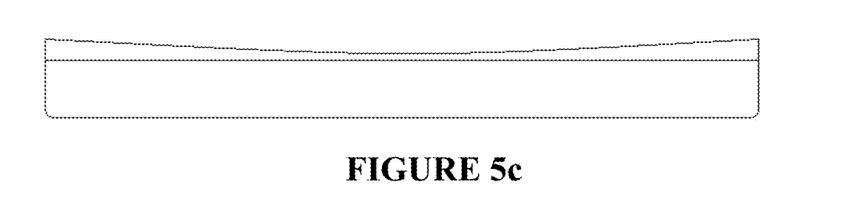
Figure 5D:
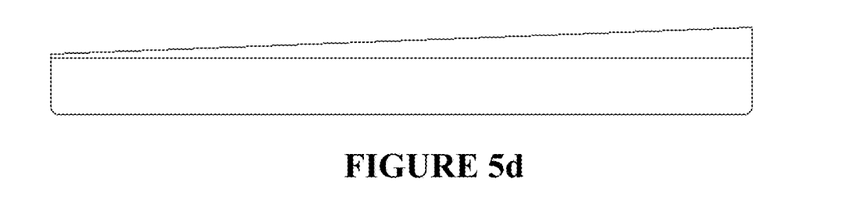

Other examples of sensor configurations are shown in FIGS. 5a-d. A substantially round sensor may have a single continuous chamber (FIG. 5a) or multiple chambers (FIG. 5b). In either case, the sensor may include a permeability/blocking member that is thinner at the center than at the edges (FIG. 5c) or thinner at one edge (FIG. 5d), resulting in a permeability gradient as described above. The reader device may capture an image of the sensor and analyze the image to determine one or more representative values for the target analyte(s). Here, the reader device may select and/or analyze one or more analysis regions based on color, intensity, distance from the center/edge, and/or orientation on the sensor.

Referring to FIG. 5a, a sensor assembly may have one or more orientation marks 599. Orientation marks 599 may have any suitable shape, size, color, or location, and may be provided on any component or portion of an implantable sensor (e.g., to base/body 503, chamber 507, a permeability/blocking member, and/or any other component). Orientation members 599 may be used by the reader device to determine the location of an analysis region on the sensor, to orient a captured image with regard to a reference image or pre-determined pattern, and/or to select an area for image capture. The reader device may determine a detection range for an analysis region based on its position relative to one or more of orientation marks 599, the center or edge of the sensor, and/or another feature of the sensor. While FIG. 5a shows orientation marks 599 on a sensor assembly with a single continuous chamber, orientation marks may be provided with any implantable sensor and used in a variety of ways. For example, the user or the reader device may view the orientation marks to confirm that the sensor is inserted in the correct orientation or to the correct depth. Orientation marks may also provide a calibration standard for the reader device to assess, and compensate for, variations in skin tone, skin translucence, or implantation depth.

The reader device may select one or more of the analysis regions based on color, intensity of emission, prior readings, programmed instructions, and/or a pre-determined pattern or reference image. For example, the reader device may select analysis regions in a captured or real-time image based at least on a pre-determined pattern of areas for analysis. Optionally, the reader device may increase or decrease the size of a selected area based on image resolution (e.g., select a larger area where image resolution falls below a minimum threshold). The reader device may access a look-up table or database that provides detection ranges for some or all of the pre-determined analysis regions and calculate a representative value for an analyte based on the image data and corresponding detection ranges. In some examples, the reader device may select an analysis region that differs from a pre-determined analysis region in size/area, contour, and/or location. The reader device may extrapolate a detection range for this analysis region based at least on the difference (s), the pre-determined pattern, and the corresponding detection ranges provided in the look-up table or database.

Optionally, the reader device may compare two, three, or more than three selected areas or analysis regions to determine whether a portion of the sensor is exhibiting a response that is inconsistent with the response of another portion of the sensor. The inconsistency may be, for example, a difference in response time, a difference in color, or a difference in intensity. The reader device may use the comparison to determine that the sensor is leaking or otherwise malfunctioning, determine a time frame for replacement of the sensor, or engage in error correction or data smoothing to determine a representative value.

Figure 6:
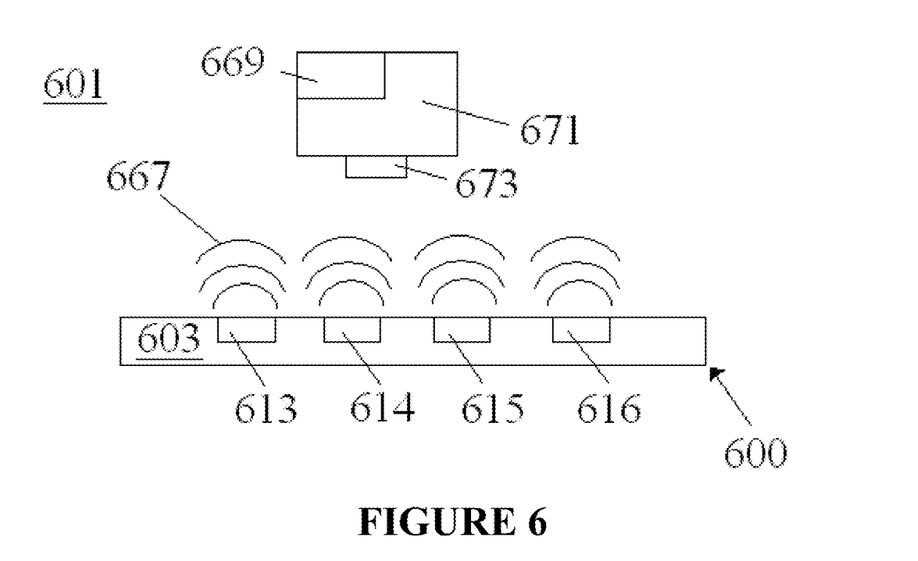
FIG. 6 shows a block diagram of an analyte detection system in accordance with various embodiments.

FIG. 6 shows a block diagram of an analyte detection system in accordance with various embodiments. An analyte detection system 601 may include an implantable sensor 600 and a reader device 671. Implantable sensor 600 may be configured with one or more modifications of the analyte reagent system(s), permeability/blocking member(s), base, and/or body to provide analysis regions with contiguous detection ranges and coextensive ranges of response. Sensor 600 may be configured to be implanted at least partially within the dermis of a subject.

Reader device 671 may include an optical sensor 673 and a non-transitory computer-readable storage medium 669. Optical sensor 673 may be configured to detect electromagnetic radiation 667 reflected, deflected, or emitted from sensor 600. Reader device 671 may analyze the detected responses of analysis regions 613, 614, 615, and 616 to one or more target/control analytes as discussed above. Non-transitory computer-readable storage medium 669 may be programmed with an algorithm to determine a representative value of a target analyte based at least in part on the wavelengths or intensity of electromagnetic radiation detected from two or more of the analysis regions. Optionally, reader device 671 may be a mobile device such as a camera, a PDA, a laptop, a tablet, or a wireless/cellular phone. Alternatively, the sensor may be read visually by a user without a separate reader device.

Implantable sensors may be produced individually or in bulk. A method of producing an implantable sensor may include forming one or more chambers in a base/body material, placing a first analyte reagent system and a second analyte reagent system into the chamber(s), and coupling one or more permeability/blocking members to the chamber (s). The first and the second analyte reagent systems and the corresponding permeability/blocking members may form portions of a first and a second analysis region, respectively, and may have contiguous detection ranges and substantially coextensive ranges of response. In some examples, the first and second reagent systems are disposed in a first and a second chamber, respectively.

The base/body material may include a reflective material. Optionally, the method may further include coating the base/body material with the reflective material. Optionally, the base/body material may be a sheet of material and the method may further include forming a third and a fourth chamber in the base material, placing a third and a fourth reagent system into the third and fourth chambers, respectively, and cutting the base material between the second and the third chambers to separate a first sensor with the first and second chambers from the sheet of material. The base material and the one or more permeability/blocking members may form a stack, and the method may further include cutting the one or more permeability/blocking members between the second and the third chambers. The base material and/or permeability/blocking members may be cut by a laser or a blade.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. An analyte sensor, comprising:
   a base configured to be retained at least partially in a subject's dermis, wherein the base is solid and impermeable, and having a thickness, an upper surface and an opposite lower surface, a first end, and an opposite second end, the base defining a first chamber disposed therein, the first chamber extending partially through the thickness of the base; and
   a first and a second analysis region coupled to the base, the first analysis region comprising a first analyte reagent system and the second analysis region comprising a second analyte reagent system,
   wherein the first and the second analysis regions have contiguous first and second detection ranges, respectively, for a target analyte, and substantially coextensive ranges of response, the first and second analysis regions configured to exhibit different responses within said coextensive ranges upon exposure to a given concentration of the target analyte and the first analyte reagent system disposed in the first chamber.

2. The analyte sensor of claim 1, further comprising one or more membranes coupled to the base, the one or more membranes being permeable to a target analyte.

3. The analyte sensor of claim 2, wherein the one or more membranes includes a first membrane portion and a second membrane portion, wherein the permeability of the first membrane portion to the target analyte is greater than the permeability of the second membrane portion to the target analyte.

4. The analyte sensor of claim 1, the base further defining a second chamber disposed therein, the second chamber extending partially through the thickness of the base, the second analyte reagent system disposed in the second chamber.

5. The analyte sensor of claim 1, the second analyte reagent system disposed in the first chamber.

6. The analyte sensor of claim 1, wherein the first and second analyte reagent systems are configured to exhibit corresponding first and second colors upon exposure to the given concentration of the analyte, said first and second colors being different colors.

7. The analyte sensor of claim 6, wherein at least one of the first and second colors is a color in the infrared range.

8. The analyte sensor of claim 1, wherein the first analyte reagent system and the second analyte reagent system have different chemical compositions.

9. The analyte sensor of claim 1, wherein the analyte sensor has a total thickness of 30-90 μm.

10. The analyte sensor of claim 1, wherein the analyte sensor has total thickness of 10 um-1 mm.

11. The analyte sensor of claim 1, wherein the analyte sensor has a total thickness of 50 μm or less.

12. The analyte sensor of claim 1, wherein the analyte sensor is configured to be retained in the dermis of a subject for at least one minute.

13. The analyte sensor of claim 1, wherein the analyte sensor is configured to be retained within the dermis of a subject for at least one month.

14. The analyte sensor of claim 1, wherein the base comprises a polymer material and $TiO_2$.

15. The analyte sensor of claim 14, wherein the polymer material comprises a polyimide.

16. The analyte sensor of claim 1, wherein each of the first and the second analyte reagent systems includes at least one detection reagent and at least one indicator.

17. The analyte sensor of claim 16, further including a plurality of beads coupled to the base, wherein one or more of the detection reagent and the indicator are immobilized on the beads.

18. The analyte sensor of claim 17, the base further defining a second chamber therein, wherein one or more reagents of the first reagent system are deposited onto a first group of the beads and one or more reagents of the second reagent system are deposited onto a second group of the beads, and the beads are positioned within at least one of the first and second chambers.

19. The analyte sensor of claim 18, wherein the first and second groups of beads are disposed within one of the first and second chambers.

20. The analyte sensor of claim 16, wherein the detection reagent is configured to interact with the target analyte to cause a change in pH, and the indicator includes a pH sensitive dye configured to produce a color change in response to the change in pH.

21. The analyte sensor of claim 16, wherein the indicator includes two or more of a lipophilic anion, a chromoionophore, and an ionophore, and the detection reagent includes an enzyme.

22. The analyte sensor of claim 13, wherein a first portion of the analyte sensor is configured to be retained within the dermis of a subject and a second portion of the analyte sensor is configured to be retained externally or within the epidermis of the subject.

23. The analyte sensor of claim 1, wherein the base comprises a reflective material.

24. The analyte sensor of claim 16, wherein the detection reagent comprises glucose oxidase.

25. The analyte sensor of claim 1, wherein the analyte sensor further comprises a first component coupled to at least the first and second analysis regions, the first component configured to provide a first gradient between the first and second analysis regions.

26. The analyte sensor of claim 25, wherein the first component is a membrane or gel layer and the first gradient is a permeability gradient resulting from variations in pore size, thickness, hydrophobicity, or reagent content of the first component.

27. The analyte sensor of claim 25, wherein the analyte sensor further comprises a second component coupled to at least the first and second analysis regions, the second component configured to provide a second gradient that extends transverse to the first gradient.

28. The analyte sensor of claim 27, wherein the second component is a membrane or gel layer and the second gradient is a result of variations in pore size, thickness, hydrophobicity, or reagent content of the second component.

29. The analyte sensor of claim 27, wherein the analyte sensor has a second permeability gradient that extends transverse to the first permeability gradient, the second permeability gradient formed by variations in reagent content or buffering systems among the first and second analyte reagent systems.

30. The analyte sensor of claim 1, the analyte sensor further comprising a third analysis region, the first, second, and third analysis regions having substantially coextensive ranges of response.

31. The analyte sensor of claim 30, wherein the third analysis region has a third detection range that overlaps the second detection range, the third analysis region configured to detect the target analyte.

32. The analyte sensor of claim 30, wherein the third analysis region is configured to detect a second analyte.

\* \* \* \* \*